United States Patent [19]
Pan et al.

[11] Patent Number: 5,891,422
[45] Date of Patent: Apr. 6, 1999

[54] ANTIMICROBIAL COMPOSITION CONTAINING A $C_3$-$C_6$ ALCOHOL

[75] Inventors: Pauline Pan, Morris Plains; Edward Carlin, Secaucus; R. Michael Buch, Randolph; Frank Volpe, Kinnelon; Alain Martin, Ringoes, all of N.J.

[73] Assignee: Warner-Lambert Company, Morris Plains, N.J.

[21] Appl. No.: 722,450

[22] Filed: Oct. 10, 1996

[51] Int. Cl.[6] .................................. A61K 7/16; A61K 7/26
[52] U.S. Cl. ................................. 424/49; 424/58
[58] Field of Search .......................................... 424/49–58

[56] References Cited

U.S. PATENT DOCUMENTS

| | | |
|---|---|---|
| 3,876,759 | 4/1975 | Pensak et al. . |
| 3,947,570 | 3/1976 | Pensak et al. . |
| 3,992,519 | 11/1976 | Hofmann et al. . |
| 4,132,770 | 1/1979 | Barth . |
| 4,420,471 | 12/1983 | Elton et al. . |
| 4,547,361 | 10/1985 | Steltenkamp et al. . |
| 4,894,220 | 1/1990 | Nabi et al. . |
| 4,900,721 | 2/1990 | Bansemir et al. . |
| 5,213,615 | 5/1993 | Michl . |
| 5,256,401 | 10/1993 | Duckenfield et al. . |
| 5,292,528 | 3/1994 | Mori et al. . |
| 5,302,373 | 4/1994 | Giacin et al. . |
| 5,405,603 | 4/1995 | Mackles et al. . |
| 5,407,662 | 4/1995 | Mackles et al. . |
| 5,472,684 | 12/1995 | Nabi et al. . |
| 5,547,657 | 8/1996 | Singleton et al. . |

FOREIGN PATENT DOCUMENTS

| | | |
|---|---|---|
| 382310 | 2/1987 | Australia . |
| 546627 | 6/1993 | European Pat. Off. . |
| 575137 | 12/1993 | European Pat. Off. . |
| 579383 | 1/1994 | European Pat. Off. . |
| 2280363 | 2/1976 | France . |
| 3113450 | 10/1982 | Germany . |
| 3702983 | 12/1987 | Germany . |
| 3634697 | 4/1988 | Germany . |
| 4418796 | 12/1994 | Germany . |
| 9408558 | 4/1994 | WIPO . |
| 9416674 | 8/1994 | WIPO . |
| 9517159 | 6/1995 | WIPO . |
| 9534276 | 12/1995 | WIPO . |
| 9534277 | 12/1995 | WIPO . |
| 9615770 | 5/1996 | WIPO . |
| 9616633 | 6/1996 | WIPO . |

*Primary Examiner*—Shep K. Rose
*Attorney, Agent, or Firm*—Jean B. Barish; Evan J. Federman

[57] ABSTRACT

An antimicrobial composition containing an alcohol having 3 to 6 carbon atoms which effectively increases antimicrobial activity and particularly a mouthwash composition that is useful in the prevention and reduction of bad breath, plaque and related gum diseases having an antimicrobially effective amount of one or more active essential oils; from about 0.01% to about 30.0% v/v of an alcohol having 3 to 6 carbon atoms; optionally, ethanol; at least one surfactant; and water. The actives not only provide enhanced efficacy but are completely solubilized, thus providing an aesthetically appealing product.

13 Claims, No Drawings

ANTIMICROBIAL COMPOSITION CONTAINING A $C_3$-$C_6$ ALCOHOL

BACKGROUND OF THE INVENTION

1. Field of the Invention

The invention relates generally to antimicrobial compositions containing a $C_3$–$C_6$ alcohol and particularly oral compositions, such as but not limited to liquids, pastes and gels for the prevention and elimination of bad breath as well as for the reduction of oral microorganisms responsible for the development of dental plaque, gingivitis, and tooth decay. A preferred embodiment of the present invention relates to a $C_3$–$C_6$ alcohol-containing, reduced ethanol or ethanol-free mouthwash that is effective in preventing those problems.

2. Description of Related Art

The effectiveness of an antimicrobial composition is dependent upon the ability of the composition to deliver the antimicrobial agent(s) contained therein to the desired microbial target(s). This is particularly so for antimicrobial oral compositions where the exposure time of the target microbes to the antimicrobial agent is generally of a short duration.

Oral compositions, such as mouthwashes, have been used by people for many years for the prevention of bad breath and for the elimination of bacteria and other oral microorganisms that are responsible not only for bad breath but also tooth decay, plaque and gum diseases such as gingivitis and periodontitis. To this end, antiseptic mouthwashes in the past have been designed to clean the oral cavity, provide fresh breath and kill these pathogenic microbes.

The leading antiseptic mouthwash has always contained ethanol at a level of 26.9% by volume, based on the total mouthwash volume (hereinafter referred to as "% v/v"). Ethanol is used both as a delivery vehicle and as a solvent in which the active ingredients, and additives such as astringents, color additives, flavor oils, and the like, can be dissolved and then dispersed into solution. Ethanol also enhances the flavor oil organoleptic cues.

However, the use of high levels of ethanol in consumer health products has been recently challenged from an overall health standpoint. Merely reducing the levels of ethanol in these mouthwash compositions has significant disadvantages. It has been found that lower ethanol levels result not only in a loss in the solubility of the actives and other ingredients in the composition, but there is also a noticeable decrease in the ability of the composition to kill the oral microorganisms responsible for bad breath, plaque and gum disease. This loss in antimicrobial activity is believed to be a result of less favorable antimicrobial agent kinetics due to the reduction of ethanol as a vehicle. Antimicrobial agent kinetics affects the rate at which an antimicrobial agent will diffuse from the delivery system and penetrate the dental plaque matrix. Thus, the delivery system of an antimicrobial composition should provide favorable antimicrobial agent kinetics to enhance efficacy, particularly when a composition, e.g. a mouthwash composition, is only applied for a short duration. Heretofore, fairly high levels of ethanol have been required to provide the desired antimicrobial kinetics, particularly for compositions containing antimicrobially effective amounts of essential oils.

There is a substantial need for the development of oral compositions, such as a mouthwash, having a reduced ethanol delivery system with favorable antimicrobial agent kinetics and in which the antimicrobial agents are completely dissolved so that the composition continues to be effective in the prevention of bad breath, the killing of oral microbes and the resultant penetration, reduction or elimination of plaque and gingivitis. Thymol is a well known antiseptic agent, also known as an essential oil, which is utilized for its antimicrobial activity in a variety of mouthwash preparations. In particular, thymol can be utilized in oral hygiene compositions such as mouth rinses in sufficient quantities to provide desired beneficial therapeutic effects. LISTERINE®-brand mouthwash is a well-known antiseptic mouthwash that has been used by millions of people for over one hundred years and has been proven effective in killing microbes in the oral cavity that are responsible for plaque, gingivitis and bad breath. Thymol and other essential oils, such as methyl salicylate, menthol and eucalyptol, are active ingredients (e., antimicrobial agents) in antiseptic mouth rinses such as LISTERINE®. These oils achieve their efficacy although present in small amounts. Without being restricted to any specific theory, it is now believed that the efficacy and taste of antiseptic mouthwashes such as Listerine® may be due to the dissolution and delivery kinetics of these four active ingredients. Dissolution is also important from an aesthetic point of view since a clear mouthwash solution is certainly preferred by consumers to one that is cloudy, turbid or heterogeneous.

Mouthwash compositions containing ethanol or isopropanol or a mixture of both are known. For example, U.S. Pat. No. 3,947,570 discloses a mouthwash composition having 0.01 to about 1% by weight, based on the total weight of the composition (hereinafter referred to as "% w/w"), of lemon oil flavoring, 0 to about 25, preferably 5 to 24% w/w of a nontoxic alcohol such as isopropanol and ethanol, about 0.1 to 5% w/w of a non-ionic surfactant and 60 to 95% w/w water. The alcohol may be denatured with flavoring agents, generally in an amount between about 1 and 2 percent of the total amount of alcohol in the composition. The disclosed flavoring agents include anethole, anise oil, bay oil, benzaldehyde, bergamot oil, bitter almond, camphor, cedar leaf oil, chlorothymol, cinnamic aldehyde, cinnamon oil, citronella oil, clove oil, coal tar, eucalyptol, eucalyptus oil, eugenol, guaiacol, lavender oil, menthol, mustard oil, peppermint oil, phenol, phenyl salicylate, pine oil, pine needle oil, rosemary oil, sassafras oil, spearmint oil, spike lavender oil, storax, thyme oil, thymol, tolu balsam, turpentine oil, wintergreen oil and boric acid.

U.S. Pat. No. 5,292,528 is directed to an oral composition containing 0.001% to 50% w/w of an organosilicone-type quaternary ammonium salt immobilized in a water insoluble solid cairier and at least one surfactant of either 0.01% to 15% w/w polyoxyethylene-polyoxypropylene block copolymer or 0.001% to 50% w/w of alkoxyamide. The composition may also contain 0.01% to 20% w/w of a thickening agent and preferably at least one alcohol selected fiom the group consisting of ethanol, propanol and isopropanol in an amount of about 0.01% to 60% w/w. This reference exemplifies a composition containing an immobilized quaternary ammonium salt, chlorohexidine gluconate and a mixture of ethanol and isopropanol. The reference also discloses that flavoring agents, such as various essential oils, may be used if desired.

U.S. Pat. No. 4,132,770 discloses a mouthwash composition containing about 3 to 9% w/w baking soda, 0 to about 20%, preferably about 5 to 15% w/w of a nontoxic cosmetic alcohol such as ethanol or isopropanol, about 0.5 to 4.0% w/w of a non-ionic surfactant and 60 to 95% w/w water. The alcohol preferably contains a flavor oil, such as those listed above, in an amount of about 0.05–0.4% w/w.

U.S. Pat. No. 5,302,373 describes a concentrated mouthwash formula having 5 to 50% w/w ethanol, 2 to 30% w/w alkali metal bicarbonate, 0.5 to 30% w/w humectant and 5 to 35% w/w water. The composition may also contain up to about 3% w/w hydrophilic polymer and up to about 5% w/w surfactant. This reference discloses that part or all of the ethanol can be substituted by a nontoxic cosmetic monohydric alcohol, such as isopropanol. Other optional components that may be present in the composition include, among others, thymol, as a bactericide, and flavorants such as oils of spearmint, peppermint, wintergreen, sassafras, clove, sage, eucalyptus, cinnamon, lemon, orange and methyl salicylate. These references do not exemplify or suggest the advantage of employing a $C_3$ to $C_6$ aliphatic alcohol with an antimicrobial effective amount of one or more essential oils.

Other prior art references have broadly disclosed, but not exemplified, substituting lower alkyl mono- or dihydric-alcohols for ethanol in various mouthwash formulations. For example, U.S. Pat. No. 5,256,401 describes a mouthwash composition having a water-alcohol mixture with a weight ratio in excess of 10:1 and about 0.01 to about 0.9% w/w of a noncationic antibacterial agent, such as triclosan. The alcohol may be a non-toxic alkyl mono- or dihydric alcohol, such as ethanol, n-propanol, isopropanol or propylene glycol, although only ethanol is exemplified. The prefelTed antimicrobial agents include triclosan, phenol, thymol, eugenol, 2,2-methylene bis (4-chloro-6-bromophenol), nerolidol and bisabolol. The use of the phenolic compounds, however, is not exemplified. It is also disclosed that surface active agents are desirable and that flavor oils may be employed, The antimicrobial is solubilized in a low amount of alcohol by using low concentrations of the antimicrobial in the composition.

Clearly, there is still a need for an antimicrobial composition having a delivery system capable of enhanced antimicrobial agent kinetics so as to provide effective antimicrobial treatment even when the duration of the treatment is short. Moreover, there is a particular need for a reduced ethanol or ethanol-free composition that is highly efficacious in the prevention of bad breath, plaque and gum disease. In addition, there is a need for such oral compositions that both kill the oral microflora responsible for these problems and clean the oral cavity leaving a finesh, lubricous mouthfeel.

SUMMARY OF THE INVENTION

The present invention, in its broadest sense, is an antimicrobial composition containing an alcohol having 3–6 carbon atoms. A preferred embodiment of this invention relates to an antimicrobial mouthwash composition, particularly one having a reduced ethanol content or being substantially free of ethanol. The oral compositions of this invention provide a high level of efficacy in the prevention of plaque, gum disease and bad breath. In addition, the oral mouthwash compositions of this invention are clear, aesthetically appealing products.

Significantly, it has been unexpectedly discovered that antimicrobial compositions with alcohols having 3 to 6 carbon atoms result in compositions that have antimicrobial agent kinetics substantially equivalent to and even superior to compositions with high level ethanolic delivery systems. This result is highly unexpected since it was believed that the diffusion of the antimicrobial agent in compositions with alcohols having a molecular weight greater than ethanol would be slower, thereby reducing the effectiveness of that agent. Preferred alcohols having 3 to 6 carbon atoms are aliphatic alcohols. A particularly preferred aliphatic alcohol having 3 carbons is 1-propanol. 1-Propanol unexpectedly shows enhanced antimicrobial agent kinetics compared to ethanolic delivery systems.

A first embodiment of this invention is an antimicrobial composition comprising (a) an antimicrobially effective amount of thymol and one or more other essential oils, (b) from about 0.01% to about 70.0% v/v, preferably about 0.1% to about 30% v/v, more preferably about 0.1% to about 10% v/v and most preferably about 0.2% to about 8% of an alcohol having 3 to 6 carbon atoms and (c) a vehicle. The preferred alcohol is 1-propanol. The vehicle may be a solid or a liquid. The liquid vehicle can be aqueous or nonaqueous, and may include thickening agents or gelling agents to provide the compositions with a particular consistency. Water and water/ethanol mixtures are the preferred vehicle.

Another embodiment of the present invention is directed to an antimicrobial composition comprising (a) an antimicrobially effective amount of an antimicrobial agent, (b) from about 0.01% to about 70% v/v, preferably about 0.1% to about 30% v/v, more preferably about 0.2% to about 8% v/v of propanol and (c) a vehicle. The antimicrobial composition of this embodiment exhibits unexpectedly superior delivery system kinetics compared to prior art ethanolic systems. Exemplary antimicrobial agents which may be employed include, without limitation, essential oils, cetyl pyidium chloride (CPC), chlorhexidine, hexetidine, chitosan, triclosan, hydrogen peroxide, domiphen bromide, carbamide peroxide, stannous fluoride, soluble pyrophosphates, metal oxides including but not limited to zinc oxide, peppermint oil, sage oil, sodium bicarbonate, sanguinaria, dicalcium dihydrate, aloe vera, polyols, protease, lipase, amylase, and metal salts including but not limited to zinc citrate, and the like. A particularly preferred aspect of this embodiment is directed to an antimicrobial oral composition and most preferably a mouthwash having up to about 30% v/v, preferably up to about 10% v/v, and most preferably up to about 3% v/v 1-propanol.

Yet another embodiment of the present invention provides a reduced ethanol, antimicrobial mouthwash composition which comprises (a) an antimicrobial effective amount of thymol and one or more other essential oils; (b) from about 0.01 to about 30.0% v/v, preferably about 0.1% to about 10% v/v, and most preferably 0.2% to about 8% v/v of an alcohol having 3 to 6 carbon atoms; (c) ethanol in an amount of up to about 25% v/v; (d) at least one surfactant; and (e) water. Preferably the total concentration of ethanol and alcohol having 3 to 6 carbon atoms is no greater than 30% v/v, more preferably no greater than 25% v/v, and most preferably no greater than 22% v/v.

Another aspect of this invention is directed to the discovery that the plaque penetration efficacy of a reduced ethanol mouthwash composition containing a $C_3$–$C_6$ alcohol and a surfactant improves as the weight ratio of surfactant to $C_3$–$C_6$ alcohol decreases. Thus, preferably, the compositions of this invention contain an amount of at least one surfactant to provide a weight ratio of surfactant to $C_3$–$C_6$ alcohol of less than 0.6, preferably a weight ratio less than 0.5, and most preferably a weight ratio less than 0.4. Preferably the surfactant is a poloxamer surfactant, most preferably poloxamer 407.

In still another embodiment, the present invention provides an ethanol-free antimicrobial mouthwash composition which comprises (a) an antimicrobial effective amount of thymol and one or more other essential oils; (b) from about 0.01% to about 30.0% v/v, preferably about 0.1% to about 10% v/v, and most preferably about 0.2% to about 8% of an alcohol having 3 to 6 carbon atoms; (c) at least one surfactant; and (d) water.

The alcohol having 3 to 6 carbon atoms is preferably selected from the group consisting of 1-propanol, 2-propanol, 1-butanol, 2-butanol, tert-butanol and corresponding diols. 1-Propanol and 2-propanol are preferred and with 1-propanol being most preferred.

DETAILED DESCRIPTION OF THE INVENTION

The antibacterial compositions of the present invention provide an unexpected high degree of antiseptic efficacy towards microorganisms and particularly oral microorganisms responsible for oral malodor and the build-up of plaque and calculus and the resulting tooth and gum diseases that may follow.

The antimicrobial compositions of the present invention can be topical or oral compositions. Oral compositions, which are preferred, may be selected, for example, from the group consisting of mouthwash, toothpaste, tooth powder, dental cream, dental floss, liquids, gels, chewing gum, liquid center filled gums, mints, lozenges, and the like. Although one preferred aspect of the present invention is directed to an antimicrobial composition containing 1-propanol and an antimicrobial agent, a particularly preferred aspect of the invention includes an oral composition, most preferably a mouthwash, containing an alcohol having 3 to 6 carbon atoms and an antimicrobial agent selected from thymol and/or other essential oils.

The oral compositions of the present invention exhibit enhanced antimicrobial efficacy even with reduced ethanol content or when they are ethanol-free. Although the exact mechanism of action is unknown, enhanced antimicrobial efficacy is obtained when minor amounts of thymol and/or one or more other essential oils (e.g., eucalyptol, menthol and methyl salicylate) are combined with about 0.01% to about 30% v/v of an alcohol having 3 to 6 carbon atoms. More preferably the alcohol having 3 to 6 carbon atoms is employed in an amount of from about 0.1% to about 10% v/v and most preferably from about 0.2% to about 8% v/v. The preferred alcohol is 1-propanol or 2-propanol, with 1-propanol being highly preferred.

Thymol, $(CH_3)_2CHC_6H_3(CH_3)OH$ (isopropyl-m-cresol), is only slightly soluble in water but is soluble in alcohol, and its presence is one of the reasons ethanol was necessary in the well-established, high ethanol commercial mouthwashes such as LISTERINE®. Methyl salicylate, $(C_6H_4OHCOOCH_3)$, also known as wintergreen oil, additionally provides flavoring to the mouthwash together with its antimicrobial function. Eucalyptol ($C_{10}H_{18}O$; cineol) is a terpene ether and provides a cooling, spicy taste and antiseptic activity. Menthol ($CH_3C_6H_9(C_3H_7)OH$; hexahydrothymol) also is only slightly soluble in alcohol, is fairly volatile, and in addition to any antiseptic properties provides a cooling, tingling sensation.

In the oral compositions, the essential oils are used in amounts effective to provide antimicrobial activity in the oral cavity. Generally, the total amount of essential oils present in a mouthwash composition of this invention can be from about 0.001% to about 0.35% w/v, with about 0.16% to about 0.28% w/v being preferred. Amounts employed in other oral compositions and topical compositions will generally be greater and can be readily ascertained by those skilled in the art. The compositions of the present invention generally contain thymol and/or one or more other essential oils. Preferably the additional essential oils are eucalyptol, menthol, or methyl salicylate, or mixtures thereof. Most preferably, the composition contains all four of these essential oils.

Thymol is preferably employed in the mouthwash composition of this invention in amounts of from about 0.001% to about 0.35% w/v, and most preferably from about 0.04% to about 0.07% w/v. Eucalyptol is preferably employed in amounts of from about 0.001% to about 0.2% w/v, and most preferably from about 0.085% to about 0.10% w/v. Menthol is preferably employed in amounts of from about 0.001% to about 0.35% w/v and most preferably from about 0.035 to about 0.05% w/v. Methyl salicylate is preferably employed in amounts of from about 0.001% to about 0.30% w/v, and most preferably from about 0.04% to about 0.07% w/v.

The mouthwash compositions of this invention, containing thymol and/or at least one other essential oil provide effective antimicrobial activity without the presence of other types of antimicrobial agents. For example, such compositions do not require known antimicrobial halogenated diphenyl ethers, such as triclosan and the like, to achieve effective antimicrobial activity. However, other antimicrobial agents may be present if desired.

When the alcohol having 3 to 6 carbon atoms is 1-propanol the composition may employ one or more of the above-described essential oils or any other antimicrobial agent that is antimicrobially effective. Such exemplary antimicrobial agents include chlorhexidine, chitosan, triclosan, cetyl pyridium chloride, domiphen bromide and the like. The amount of such antimicrobial agents employed in the composition of this invention can readily be determined by those skilled in the art. The vehicle for the antimicrobial compositions of this invention, and particularly for the essential oils containing compositions, may be an aqueous medium. The aqueous medium may be a water-alcohol mixture, generally a water-ethanol mixture. Alternatively, in the case of ethanol-free compositions, the aqueous medium is water. In the past, most antiseptic oral mouthwash compositions, such as LISTERINE®-brand mouthwashes, required high ethanol levels of up to about 27% v/v. These levels of ethanol were necessary for the antimicrobial agents to be acceptably effective as well as to provide a clear, aesthetically attractive liquid medium. Merely reducing the ethanol levels, without more, results in a cloudy, less effective product.

Without being bound to any theory, it is believed that in high ethanol oral compositions, the ethanol completely solubilizes the antimicrobial actives. In so doing, the antimicrobial actives are more readily dispersed throughout the solution, and favorable antimicrobial agent kinetics are achieved to foster attack of the pathogenic microbes throughout the oral cavity. Reducing the ethanol levels was believed to adversely affect antimicrobial agent kinetics.

In accordance with the present invention, however, it was surprisingly and unexpectedly found that ethanol may be used at reduced levels, or may even be completely removed, without sacrificing antimicrobial efficacy or clarity if the oral composition, particularly the mouthwash composition, also contains an alcohol having 3 to 6 carbon atoms. "Reduced level" of ethanol means an amount of ethanol up to about 25% v/v, such as an amount of from about 0% v/v to about 25% v/v, preferably no more than about 22% v/v (e.g., from about 0% to about 22% v/v). A favorable amount of ethanol for enhancement of the organoleptic cues of the mouthwash compositions of this invention is in the range of from about 20% v/v to about 22% v/v, although lesser amounts (e.g. 15% v/v) may be used if desired. "Ethanol-free" means that the composition is substantially free of ethanol.

It has also surprisingly been found that the antimicrobial activity of reduced alcohol or alcohol free oral compositions is equal to or better than the antimicrobial activity of high alcohol (i.e., approximately 27% v/v ethanol) oral compositions when $C_3$–$C_6$ alcohol and small amounts of surfactant are used together in the reduced alcohol and alcohol free compositions of this invention.

A convenient reference point for measuring antimicrobial activity is that of LISTERENE®-brand mouthwash, which contains about 27% v/v ethanol. As explained in detail below, the antimicrobial activities of the mouthwash compositions of this invention are expressed as "R-factors." An "R-factor" is the ratio of the time necessary for an inventive composition to effectively kill typical oral cavity microbes in an in vitro biofilm, to the in vitro kill time of a standard high alcohol mouthwash. For example, if a composition has an "R-factor" of 1.0, its in vitro kill time is the same as that of the standard high alcohol mouthwash. The mouthwash compositions of the present invention exhibit an R-factor of less than about 1.2, and most preferably less than about 1.0.

Surface active agents (surfactants) may be employed in the compositions of the present invention. They are organic materials which aid in the complete dispersion of the ingredients throughout the solution as well as dispersing the preparation throughout the oral cavity. Preferably, the surfactant used in the compositions of the present invention is a non-ionic surfactant or anionic surfactant employed in an amount sufficient to help solubilize the actives. By sufficient amount it is meant that the surfactant is present in an amount that effectively assists in the solubilization and delivery system kinetics of the essential oils.

If a non-ionic surfactant is employed, then it is preferable to keep the weight ratio of non-ionic surfactant to $C_3$–$C_6$ alcohol less than about 0.8. More preferably, the weight ratio should be less than about 0.7 and most preferably below about 0.6. The weight ratio of non-ionic surfactant to $C_3$–$C_6$ alcohol may affect the plaque penetration efficacy of the mouthwash compositions of this invention. R-factor generally decreases as the above noted weight ratio decreases.

The preferred non-ionic surfactants are selected from the group known as poly(oxyethylene)-poly(oxypropylene) block copolymers. Such copolymers are known commercially as poloxamers and are produced in a wide range of structures and molecular weights with varying contents of ethylene oxide. These non-ionic poloxamers are non-toxic and acceptable as direct food additives. They are stable and readily dispersible in aqueous systems and are compatible with a wide variety of formulations and other ingredients for oral preparations. These surfactants should have an HLB (Hydrophilic-Lipophilic Balance) of between about 10 and about 30 and preferably between about 10 and about 25.

By way of example, non-ionic surfactants useful in this invention include the following poloxamers:

| | | | |
|---|---|---|---|
| 105 | 188 | 237 | 334 |
| 108 | 215 | 238 | 335 |
| 124 | 217 | 284 | 338 |
| 184 | 234 | 288 | 407 |
| 185 | 235 | 333 | |

Generally these polymers when used are present in amounts of from about 0.01% w/v to about 8.0% w/v, and preferably from about 0.01% to about 1.0% w/v. A particularly preferred poloxamer is poloxamer 407 which is incorporated in an amount of about 0.01% to 0.8% w/v.

The preferred anionic surfactants are selected from sodium lauryl sulfate, magnesium lauryl sulfate, Tauranol® and the like. Tauranol® is sodium-N-methyl-N-cocoyl taurate available from Finetex, New Jersey. Generally, the anionic surfactants when used are present in amounts of about 0.001% to about 4.0% w/v, and preferably from about 0.005% about 2.0% w/v.

The surfactant is used to help solubilize the essential oils and flavor oils which may otherwise not be soluble in these aqueous systems due to their reduced ethanol content. The surfactant(s) also act to disperse the actives and flavors throughout the solution and enable the compositions to provide a clear, uniform appearance that is aesthetically more appealing.

The essential oil methyl salicylate not only provides antimicrobial activity but, being a wintergreen flavor oil, also adds to the organoleptic flavor tones and complements the taste masking function of the peppermint oil blend.

Other flavor oils may also be added to further modify or magnify the cooling minty taste of the peppermint, or reduce or mask the sharp "bite" or "burn" of ingredients such as thymol and ethanol. Suitable flavors (and typical amounts) include spearmint oil (from about 0.001% w/v to about 0.5% w/v), oil of anise (from about 0.01% w/v to about 0.2% w/v), benzyl alcohol (from about 0.001% w/v to about 0.1% w/v) and anethole (from about 0.001% w/v to about 0.5% w/v).

Other flavors such as citrus oils, vanillin and the like may be incorporated to provide further taste variations.

The particular flavor oils and other taste-improving ingredients employed will vary depending upon the particular taste and feel desired. Those skilled in the art can select and customize these types of ingredients to provide the desired results.

Additional conventional components may be added as in mouthwashes of the prior art. Whereas some ethanol containing mouthwashes have a pH of about 7.0, reduction of the ethanol level requires the addition of acidic preservatives, such as sorbic or benzoic acid, which reduce pH levels. Buffer systems are then necessary to control the pH of the composition at optimal levels. This is generally accomplished through the addition of a weak acid and its salt or a weak base and its salt. Useful systems have been found to be sodium benzoate and benzoic acid in amounts of from about 0.01% to about 4.0% w/v, and sodium citrate and citric acid in amounts of from about 0.001% to about 0.2% w/v. Preferably the buffers are incorporated in amounts that maintain the pH at levels of from about 3.5 to about 9.0, and more preferably from about 4.0 to 7.0. Without being bound to any theory, it is believed that these pH levels provide the essential oils with an environment that also maximizes their antimicrobial activity.

Other conventional ingredients may be used in the mouthwash compositions of this invention, including those known and used in the art. For example, humectants such as polyethylene glycol may be added as an additional solubilizer for the flavor oils and to also provide texture to the composition. These are incorporated in amounts of from about 0.3% w/v to about 5.0% w/v, and enhance the lubricous mouthfeel of the mouthwash as it is used and to provide a refreshing, moist, organoleptic feeling thereafter. Glycerin may be incorporated in amounts of from about 1.0% w/v to about 16.0% w/v, and preferably in an amount of about 7.5% w/v. Sweeteners such as aspartame or sodium saccharin and the like may be added for better taste in amounts of from about 0.005% w/v to about 1.0% w/v.

Zinc compounds may be added as an astringent for an "antiseptic cleaning" feeling in an amount of from about 0.0025% w/v to about 0.75% w/v. And although the mouthwash formulations of the present invention may be formulated to be substantially clear and colorless, acceptably approved food dyes are preferably used to provide a pleasing color to the formulations of the invention. These may be selected from the long list of acceptable food dyes and. Suitable agents for this purpose include FD&C yellow #5, FD&C yellow #10 and FD&C green #3.

Water is added to q.s. the composition and the composition may then be bottled and packaged for shipping. The oral composition of the present invention is preferably a mouthwash but may also be formulated, if desired, as gels, foams, pastes, aerosols or tablets using standard formulations known in the art as appropriate.

Alternatively, the compositions of the present invention may be formulated in a chewing gum, liquid center chewing gum, semi-solid, solid or liquid concentrate form. In such embodiments, for example, water is added to q.s. the volume to the necessary total for a liquid concentrate. The composition may then have water added at a later date when ready for use. Such concentrates are advantageous for storage and shipping.

The oral compositions of this invention may also be substantially solid or pasty in character such as a dental cream, toothpaste, or a tooth powder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in tooth powder. For toothpaste and dental creams the water content is about 25% to 50% by weight.

In clear gels, a polishing agent of colloidal silica and alkali metal aluminosilicate complexes are preferred since they have refractive indicies close to the refractive indicies of gelling agent liquid systems commonly used in dentifrices.

In the oral compositions that are toothpastes, dental creams, or gels the vehicle may comprise water, typically in an amount of about 10–90% by weight of the composition. Polyethylene glycol, propylene glycol, glycerin or mixtures thereof may also be present as humectants or binders in amounts of about 20–25% by weight. Particularly advantageous liquid ingredients comprise mixtures of water with polyethylene glycol or glycerin and propylene glycol. A gelling agent (thickening agent) including natural or synthetic gums such as sodium carboxymethylcellulose, hydroxyethyl cellulose, methyl cellulose and the like may be used, in the range of about 0.5–5% by weight. In a toothpaste, dental cream or gel, the liquids and solids are proportioned to form a creamy or gelled mass which is extrudable from a pressurized container or from a collapsible tube. Topical pastes, creams and gels may also be formulated in a similar manner. The pastes or gels may also contain a surface active agent which may be an anionic, nonionic or zwitterionic detergent (surfactant) in amounts of about 0.05–5% by weight. The anionic and nonionic surfactants that are suitable have already been discussed above.

Zwitterionic surface active agents include the betaines and sulfobetaines. Typical alkyl dimethyl betaines include decyl betaine or 2-(N-decyl-N,N-dimethylammonio)acetate, coco betaine, cetyl betaine, stearyl betaine, etc. The amidobetaines similarly include cocamidoethyl betaine, cocamidopropyl betaine, lauramidopropyl betaine and the like. These sulfobetaines are similar in structure to the betaines, but have a sulfonate group in place of the carboxylate group, and include alkylsulfobetaines, alkylamidosulfobetaines and alkylaminosulfobetaines.

R-Factor

Biofilms of the microorganism *Streptococcus mutans* (ATCC #25175) grown on stainless steel wires simulate thick, semipermeable dental plaque. For purposes of the present invention, an "R-Factor" is a convenient measure of the antimicrobial efficacy of the mouthwash compositions of the present invention, as measured by their ability to kill those biofilms. The R-Factor is defined as the ratio of (1) the time, in minutes, necessary for a mouthwash composition to kill *S. mutans* microorganism biofilms grown in vitro on stainless steel wires, to (2) the time, in minutes, necessary for a standard high ethanol mouthwash composition to kill similar biofilms of the same microorganism grown in vitro on other, identical stainless steel wires. Those kill times are obtained by a plaque penetration assay developed by the present inventors.

Plaque Penetration Assay

The plaque penetration assay employed by the present inventors to obtain their biofilm critical kill times is a modification of the well-known procedure of Tanzer, et al., described or referenced in, e.g., Tanzer, et al., "Structural requirements of Guanide, Biguanide and Bisbiguanide Agents for Antiplaque Activity," *Antimicrobial Agents and Chemotherapy*, Dec. 1977, pp. 721–729; and Tanzer, et al., "In Vitro Evaluation of Seven Cationic Detergents as Antiplaque Agents," *Antimicrobial Agents and Chemotherapy*, Mar. 1979, pp. 408–414.

The high ethanol mouthwash composition employed by the present inventors as their standard for their plaque penetration assay contains 27% v/v ethanol and has the composition shown in the following Table 1:

TABLE 1

| Ingredient | Amount |
| --- | --- |
| Ethanol (USP) | 284 mls |
| Thymol | 0.64 gram |
| Eucalyptol | 0.92 gram |
| Menthol | 0.42 gram |
| Methyl Salicylate | 0.60 gram |
| Benzoic Acid | 1.5 grams |
| Caramel | 0.2 gram |
| Poloxamer 407 | 1.0 gram |
| Water | Q.S. to 1 Liter |

The media required for the plaque penetration assay include sterile deionized water; Letheen Broth (DIFCO); and Jordan's complex medium (with and without bromocresol purple pH indicator) [see Jordan, H. V. et al. *J. Dent. Res.* 39: 116–123 (1960)]. The equipment requirements for the assay include a large number of sterile glass test tubes (e.g., 13×100 millimeters); test tube racks to hold multiple rows of sample tubes; an autoclave; and stainless steel Nichrome wires (1.5×85 mm) It is convenient to attach each plaque wire to a Moiton Closure by any suitable means, such as welding.

Jordan's medium may be prepared by blending the following ingredients with heating as necessary:

| Ingredient | Amount |
| --- | --- |
| Trypticase Peptone (BBL) | 5 grams |
| Yeast Extract | 5 grams |
| $K_2HPO_4$ | 5 grams |
| Stock Salts Solution (see below) | 0.5 ml |
| Sucrose | 50 grams |
| Sodium Carbonate | 0.05 grams |
| Deionized Water | Q.S to 1 Liter |

| Stock Salts Solution | |
| --- | --- |
| Ingredient | Concentration |
| $MgSO_4$ (anhydrous) | 3.9 g/L |
| $FeCl_3.6H_2O$ | 0.4 g/L |
| $MnCl_2$ (anhydrous) | 0.12 g/L |
| Distilled water | Q.S. to 1 Liter |

The pH is adjusted to 7.1 with 5N HCl followed by cooling to room temperature, if necessary. 50 ml is removed from the batch and placed in a 100 milliliter flask. Jordan's medium with pH indicator ("recovery medium") is prepared by adding 1 ml of a 1% bromocresol purple stock solution (ie., 0.1 gram bromocresol purple in 10 mls distilled water) to 1 liter of Jordan's medium.

The culture for the assay is prepared as follows. Upon receipt, the ATCC culture is rehydrated and subcultured according to the directions supplied by the American Type Culture Collection. The subculture is streaked for purity on Brain-Heart Infusion Agar (DIFCO) and inoculated into 100 ml of sterile BHI. The agar plates are examined for purity after 14–18 hours. If acceptable, 11 ml of sterile glycerin are added to the BHI culture, vortexed and then subdivided into 1.8 ml cryogenic tubes. The cultures are then stored at –80° C.

Four days prior to an assay, a frozen vial is thawed and added to the small, 100 ml flask containing 50 ml of Jordan's medium to start the cultures used for the biofilm assay. After 14–18 hours, the contents of the small flask are decanted aseptically into 2 liters of Jordan's medium. The resulting inoculated medium is then aseptically dispensed, in 5.0 ml portions, into a number of empty sterile test tubes, each tube having a plaque wire-equipped Morton cap. The inoculated tubes are then incubated anaerobically overnight (i.e., 14–16 hours) at 37° C.

The number of test tubes will vary depending upon the number of different mouthwash samples being tested, but it will be convenient to describe an assay of a standard high ethanol mouthwash and four reduced ethanol mouthwash samples, which requires racks each holding 75 test tubes (i.e., five rows of fifteen tubes, each row comprising five sets of three tubes each). The first set of three tubes in each row is usually reserved for the standard high ethanol mouthwash, with the succeeding four sets of three tubes each in that row being reserved for the four reduced ethanol samples. There are three tubes in each set because each assay is performed in triplicate.

After the overnight incubation, the plaque wires are then transferred into fresh Jordan's medium in 75 tubes (in a second rack) and again incubated anaerobically for 24 hours at 37° C. This procedure is repeated once more. Thus, the plaque wires are cultured for 3 days, with two transfers after initial inoculation.

On the third day, just prior to the assay, five additional racks (each containing 75 sterile test tubes) are prepared: a first (assay) rack whose test tubes each contain 6 ml of the sample mouthwashes; a second (water) rack whose test tubes each contain 6 ml of sterile deionized water; third and fourth racks whose test tubes each contain 6 ml of Letheen broth rinse; and a fifth rack whose test tubes each contain 5 ml of Jordan's recovery medium. For convenience, the racks may be marked for test series identity and time (by row).

Assay Procedure: Each assay will involve triplicate testing at time points separated by one minute intervals, e., at 2, 3, 4, 5 and 6 minutes of mouthwash treatment. The first (or bottom) row of each rack corresponds to the first test time and the succeeding four rows correspond, respectively, to the next four test times. The exact time of exposure of the plaque wires to the sample mouthwashes can be varied according to the thickness of the "plaques". Ideally, the exposure period will result in positive microorganism growth in the first one or two sampling intervals of the high ethanol control group, (i.e., the first and second row) and no growth thereafter. Establishing lower and upper limits of exposure required for complete kill by the control mouthwash permits an accurate comparison of the four sample mouthwashes to this control. Mouthwash exposure takes place in a 37° New Brunswick shaking water bath (shake speed 3) and may be staggered so that the 5 time points are run concurrently, but with sufficient time to permit accurate timing and handling.

(1) To start assay, transfer one row of plaque wires to the first (bottom) row of tubes in the rack containing 6 ml of sterile water. Leave in place 2 minutes. Repeat for the next four rows of plaque wires.

(2) After the water rinse, transfer each row of plaque wires into the appropriate, corresponding, row of tubes in the rack containing 6 ml of test mouthwash. Leave each row of plaque wires in place, with shaking in the 37° water bath, for its treatment (exposure) period; i.e., remove the rows of plaque wires sequentially at 5 preset time points so that each succeeding row of plaque wires is exposed to a mouthwash for successively longer periods of time (e.g., 2, 3, 4, 5 and 6 minutes; individual timing can vary according to estimated "plaque" thickness.

(3) For each row of plaque wires, at the end of its treatment period, immediately remove the row and place it in the appropriate corresponding row of the first rack of 6 ml Letheen Broth neutralization/rinse tubes. Leave each row of wires in that broth for 5 minutes and then transfer it to the appropriate corresponding row of the second rack of 6 ml Letheen Broth rinse tubes.

(4) At the end of the second Letheen Broth rinse, remove each row of plaque wires and place it in the appropriate corresponding row of the rack of 6 ml Jordan's recovery medium (with bromocresol purple). Incubate anaerobically for 48 hours at 37° C.

(5) Read for growth (+) or no growth (–) at 48 hours. Positive growth is indicated by a color change from purple to yellow (i.e., if the microorganism is still viable, it will produce an acid which causes the color change); positive growth is often accompanied by an increase in broth turbidity.

Determination of Critical Kill Times and R-Factor: Since each mouthwash sample is located in the same set of three tubes in each row of the rack, the critical time necessary for the sample to completely kill the microorganism can be determined by observing the point (front to back or bottom to top, as the case may be) at which the Jordan recovery medium color changed from yellow to purple. The critical kill time for any sample, divided by the critical kill time for the control mouthwash in that same rack, gives the R-Factor for that sample.

Table 2 below summarizes a statistical scale developed by the present inventors which relates the observed change from growth (+) to no growth (−) to critical kill times. For example, as shown in the first row of Table 2, where the observed condition changes from growth (continuous +'s) to no growth (continuous −'s) ("no anomaly"), the critical kill time is determined by adding 0.50 minute to the time at which the last growth observation (+) was made. The balance of Table 2 sets forth how critical kill times are determined for different observed growth/no growth intervals between continuous growth segments and continuous no growth segments.

TABLE 2

BUSCH Scores For Critical Kill Times (CKT)

| Intervals between continuous +'s and −'s | Add To Last (+) Time |
|---|---|
| No anomaly | 0.50 |
| −+ | 1.50 |
| −++ | 2.90 |
| −+++ | 4.10 |
| −+−+ | 2.50 |
| −+−−+ | 2.10 |
| −++−+ | 4.06 |
| −−+ | 1.10 |
| −−++ | 2.50 |
| −−+−+ | 3.84 |
| −−−+ | 0.90 |
| −−−−+ | 0.80 |

By way of further example, consider the examples of growth/no growth sequences, and their associated critical kill times, in Table 3. In the first row of Table 3, there was no anomaly between continuous +'s and continuous −'s; therefore, CKT (per Table 2)=4.0+0.5=4.5 minutes (i.e., kill occurred somewhere between 4.0 and 5.0 minutes). In the second row of Table 3, the interval between continuous +'s and continuous −'s is −+; therefore, CKT (per Table 2)=2.0+1.5=3.5 minutes.

TABLE 3

Examples of Growth/No Growth Sequences and CKT

| Treatment Times (min) | | | | | |
|---|---|---|---|---|---|
| 2.0 | 3.0 | 4.0 | 5.0 | 6.0 | CKT |
| + | + | + | − | − | 4.5 |
| + | − | + | − | − | 3.5 |
| + | + | + | + | + | >6.5 |
| − | − | − | − | − | <2.0 |
| + | − | − | + | − | 3.1 |

In the case of rows 3 and 4 of Table 3, clearly no end point was reached. It is assumed here that kill will occur at some point in excess of 6.5 minutes (>6.5) or much below 2.0 minutes (<2.0), respectively.

Row 5 (Table 3) is an example where the kill scale is dependent on the values which are located to the left of the last + and to the right of the first −. For that particular example, CKT=2.0+1.1=3.1 minutes (per Table 2).

The following examples are provided to illustrate the present invention and its advantages. Throughout the examples, all percentages are stated as % w/v except where noted (e.g., ethanol and propanol contents are stated as % v/v).

Example 1

A reduced ethanol mouthwash composition was prepared having the following components in potable water.

| Components | % w/v |
|---|---|
| 1-Propanol | 0.25 (v/v) |
| Ethanol | 22.7 (v/v) |
| Thymol | 0.064 |
| Menthol | 0.043 |
| Methyl Salicylate | 0.066 |
| Eucalyptol | 0.092 |
| Benzoic Acid | 0.150 |
| Caramel | 0.024 |
| Poloxamer 407 | 0.50 |
| Citric Acid | 0.010 |
| Sodium Citrate | 0.030 |
| Sorbitol | 25.0 |

The composition was prepared by adding the essential oils (thymol, menthol, methyl salicylate and eucalyptol), poloxamer 407 and benzoic acid to ethanol followed by the addition of 250 ml of potable water. To that mixture was added sorbitol, caramel, sodium citrate and citric acid. The mixture was q.s. to 1000 ml with potable water.

Example 2

A reduced ethanol mouthwash composition was prepared in the same manner as Example 1, with the exception that composition contained 0.50% v/v 1-propanol.

Example 3

A reduced ethanol mouthwash composition was prepared in the same manner as Example 1, with the exception that the composition contained 1.0% v/v 1-propanol.

Example 4

A reduced ethanol mouthwash composition was prepared in the same manner as Example 1, with the exception that the composition contained 0.15% v/v poloxamer 407.

Example 5

A reduced ethanol mouthwash composition was prepared in the same manner as Example 4, with the exception that the composition contained 0.50% v/v 1-propanol.

Example 6

A reduced ethanol mouthwash composition was prepared in the same manner as Example 4, with the exception that the composition contained 1.0% v/v 1-propanol.

Comparative Example 1

A mouthwash composition was prepared in a manner similar to Example 2, with the exception that no essential oils were added.

Comparative Example 2

A mouthwash composition was prepared in a manner similar to Example 3, with the exception that no essential oils were added.

The compositions of Examples 1–6, Comparative Examples 1–2 and "Cool Mint" Listerine®-brand mouthwash product (containing thymol and other essential oils, 21.6% w/v ethanol, 17.5% w/v sorbitol, and 0.16–0.20% w/v anethole) were tested by the previously described plaque penetration assay along with the high ethanol mouthwash described in Table 1. The results obtained are set forth in Table 4.

TABLE 4

| Composition | Poloxamer 407(A) (% w/v) | 1-propanol (B) (% v/v) | wt. ratio (A):(B) | Avg R Factor (+SE) |
|---|---|---|---|---|
| Example 1 | 0.5 | 0.25 | 2.5 | 1.26 ± 0.04 |
| Example 2 | 0.5 | 0.50 | 1.25 | 1.18 ± 0.06 |
| Example 3 | 0.5 | 1.0 | 0.63 | 1.19 ± 0.08 |
| Example 4 | 0.15 | 0.25 | 0.75 | 1.16 ± 0.02 |
| Example 5 | 0.15 | 0.50 | 0.38 | 1.05 ± 0.04 |
| Example 6 | 0.15 | 1.0 | 0.19 | 1.00 ± 0.09 |

TABLE 4-continued

| Composition | Poloxamer 407(A) (% w/v) | 1-propanol (B) (% v/v) | wt. ratio (A):(B) | Avg R Factor (+SE) |
|---|---|---|---|---|
| "CoolMint" LISTERINE ® | 0.5 | — | — | 1.18 ± 0.11 |
| Comp. Ex. 1* | 0.5 | 0.50 | 1.25 | >1.80 |
| Comp. Ex. 2* | 0.5 | 1.0 | 0.63 | 2.20 |

*No essential oils added

The R-factor results shown in Table 4 illustrate that the reduced ethanol (~22% v/v) compositions of this invention provide significant plaque penetration efficacy compared to a high ethanol (26.9% v/v) composition employing the same amount of essential oil antimicrobial agents. The results also show that the antimicrobial performance improved as the weight ratio of poloxamer 407 surfactant to propanol decreased and that reduced alcohol compositions having a surfactant to propanol weight ratio of about 0.4 or less were substantially equivalent in plaque penetration efficacy with a high alcohol composition.

Comparative Example 3

A mouthwash composition was prepared in a manner similar to Example 1, with the exception that no 1-propanol was added.

Comparative Example 4

A mouthwash composition was prepared in a manner similar to Example 4, with the exception that no 1-propanol was added.

The mouthwash composition of Examples 1–6, Comparative Examples 1–4, the high ethanol mouthwash described in Table 1, "Coolmint" Listerine® and a sterile water control were evaluated for kill kinetics (w/serum) against Staphylococcus aureus (ATCC #6538), Lactobacillus casei (ATCC #4646) and Candida albicans (ATCC #18804) using the protocol the American Dental Association. The test results are set forth in Table 5 below.

TABLE 5

| | | | Kill Time (min) of (#) Samples Tested | | | | | | | | | | | |
|---|---|---|---|---|---|---|---|---|---|---|---|---|---|---|
| | | | Staphylococcus aureus (ATCC #6538) | | | | Lactobacillus casei (ATCC #4646) | | | | Candida albicans (ATCC #18804) | | | |
| Composition | Poloxamer 407 (% w/v) | 1-propanol (% v/v) | ≤0.5 min. | ≤1.0 min. | ≤2.0 min. | ≤5.0 min. | ≤0.5 min. | ≤1.0 min. | ≤2.0 min. | ≤5.0 min. | ≤0.5 min. | ≤1.0 min. | ≤2.0 min. | ≤5.0 min. |
| Ex. 1 | .5 | .25 | | | (3) | | (2) | | | | (1) | | (3) | |
| Ex. 2 | .5 | .5 | | | (3) | | (2) | | | | (2) | (1) | (2) | |
| Ex. 3 | .5 | 1.0 | | | (3) | | (2) | | | | (3) | | | |
| Comp. Ex. 1 | .5 | .5 | | | | >5.0(1) | | | | >5.0(1) | | | | >5.0(1) |
| Comp. Ex. 2 | .5 | 1.0 | | | | >5.0(1) | | | | >5.0(1) | | | | >5.0(1) |
| Comp. Ex. 3 | .5 | — | | (1) | (3) | (1) | | (2) | (2) | | (1) | (2) | | (3) |
| Ex. 4 | .15 | .25 | | (3) | (2) | | (3) | | | | (3) | (2) | | |
| Ex. 5 | .15 | .5 | (1) | (4) | | | (5) | | | | (6) | | | |
| Ex. 6 | .15 | 1.0 | (2) | (2) | (1) | | (4) | | | | (4) | | | |
| Comp. Ex. 4 | .15 | — | | (2) | (3) | (1) | | (1) | (1) | | (2) | | (3) | (1) |
| High Ethanol | .1 | — | (3) | (2) | (3) | | (8) | | | | (8) | | | |
| "Coolmint" LISTERINE ® | .5 | — | (3) | (1) | (3) | | (8) | | | | (8) | | | |
| Sterile Water | — | — | | | | >5.0(8) | | | | >5.0(8) | | | | >5.0(8) |

The test results illustrated in Table 5 indicate the significance of combining antimicrobially effective amounts of essential oils with 1-propanol, particularly at a relatively low surfactant to 1-propanol weight ratio to obtain the highly effective reduced alcohol antimicrobial mouthwash compositions of this invention.

Other variations and modifications of this invention will be obvious to those skilled in the art. This invention is not limited except as set forth in the claims.

What is claimed is:

1. A mouthwash composition comprising:
   thymol in an amount from about 0.001% to about 0.35% w/v,
   eucalyptol in an amount from about 0.001% to about 0.20% w/v,
   menthol in an amount from about 0.001% to about 0.3% w/v,
   methyl salicylate in an amount from about 0.001% to about 0.3% w/v, ethanol in an amount from about 20% v/v to about 25% v/v, a buffer system comprising sodium benzoate and benzoic acid in an amount from about 0.01% to about 4.0% w/v to achieve a pH of about 3.5 to about 9.0, a poly(oxyethylene)-poly(oxypropylene) block copolymer in an amount from about 0.01% to about 0.8% w/v, and an alcohol having 3 to 6 carbons in an amount from about 0.01% to about 10% w/v; wherein the composition has an R-factor of about 1 to about 1.26.

2. The mouthwash composition according to claim 1, wherein the alcohol having 3 to 6 carbons is in an amount from about 0.2 to about 8.0% w/v.

3. The mouthwash composition according to claim 2, wherein the alcohol having 3 to 6 carbons is in an amount from about 0.25 to about 1.0% w/v.

4. The mouthwash composition according to claim 1, wherein the alcohol having 3–6 carbons is 1-propanol.

5. The mouthwash composition according to claim 2, wherein the alcohol having 3–6 carbons is 1-propanol.

6. The mouthwash composition according to claim 3, wherein the alcohol having 3–6 carbons is 1-propanol.

7. The mouthwash composition according to claim 1, wherein the poly(oxyethylene)-poly(oxypropylene) block copolymer is in an amount from about 0.01% to about 1.0% w/v.

8. The mouthwash composition according to claim 1, wherein the thymol is in an amount from about 0.04% to about 0.07% w/v, the eucalyptol is in an amount from about 0.085% to about 0.10% w/v, the menthol is in an amount from about 0.0355% to about 0.05% w/v; and the methyl salicylate is in an amount from about 0.04% to about 0.07% w/v.

9. The mouthwash composition according to claim 1 wherein the ethanol is in an amount from about 20% v/v to about 22.7% v/v.

10. The mouthwash composition according to claim 8, wherein the alcohol having 3 to 6 carbons is in an amount from about 0.2 to about 8.0% w/v.

11. The mouthwash composition according to claim 10, wherein the alcohol having 3 to 6 carbons is in an amount from about 0.25 to about 1.0% w/v.

12. The mouthwash composition according to claim 11, wherein the alcohol having 3–6 carbons is 1-propanol.

13. A mouthwash composition comprising:

thymol in an amount from about 0.04% to about 0.07% w/v, eucalyptol in an amount from about 0.085% to about 0.1% w/v, menthol in an amount from about 0.035% to about 0.05% w/v, methyl salicylate in an amount from about 0.04% to about 0.07% w/v, ethanol in an amount from about 20% v/v to about 22.7% v/v, a buffer system comprising sodium benzoate and benzoic acid in an amount from about 0.01% to about 4.0% w/v to achieve a pH of about 3.5 to about 9.0, a poly(oxyethylene)-poly(oxypropylene) block copolymer in an amount from about 0.01% to about 0.8% w/v, and an alcohol having 3 to 6 carbons in an amount from about 0.01% to about 10% w/v; wherein the composition has an R-factor of about 1 to about 1.26.

* * * * *